(12) United States Patent  
Colby et al.

(10) Patent No.: US 8,664,386 B2
(45) Date of Patent: Mar. 4, 2014

(54) METHODS FOR PREPARING ANTI-VIRAL NUCLEOTIDE ANALOGS

(71) Applicant: Gilead Sciences, Inc., Foster City, CA (US)

(72) Inventors: Denise A. Colby, San Francisco, CA (US); Andrew Anthony Martins, Edmonton (CA); Benjamin James Roberts, San Mateo, CA (US); Robert William Scott, San Mateo, CA (US); Nicole S. White, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/573,666

(22) Filed: Oct. 3, 2012

(65) Prior Publication Data

US 2013/0090473 A1    Apr. 11, 2013

Related U.S. Application Data

(60) Provisional application No. 61/544,950, filed on Oct. 7, 2011.

(51) Int. Cl.
*C07F 9/06* (2006.01)

(52) U.S. Cl.
USPC ........................................ 544/244; 544/242

(58) Field of Classification Search
USPC .......................................... 544/242, 243, 244
See application file for complete search history.

(56) References Cited

U.S. PATENT DOCUMENTS

| | | | |
|---|---|---|---|
| 7,390,791 B2 | 6/2008 | Becker et al. | |
| 7,741,345 B2 * | 6/2010 | Cannizzaro et al. | 514/338 |
| 7,803,788 B2 | 9/2010 | Becker et al. | |
| 8,106,064 B2 * | 1/2012 | Guo et al. | 514/274 |
| 8,354,421 B2 * | 1/2013 | He et al. | 514/274 |

* cited by examiner

*Primary Examiner* — Golam M M Shameem
(74) *Attorney, Agent, or Firm* — Fitzpatrick, Cella, Harper & Scinto

(57) ABSTRACT

Methods for isolating 9-{(R)-2-[((S)-{[(S)-1-(isopropoxycarbonyl)ethyl]amino}phenoxyphosphinyl)methoxy]propyl}adenine (compound 16):

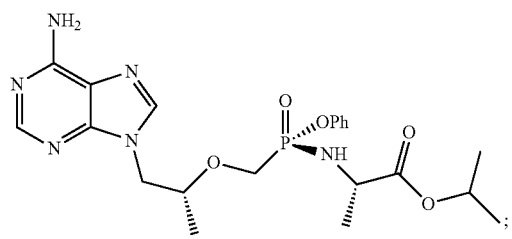

a method for preparing, in high diastereomeric purity, intermediate compounds 13 and 15:

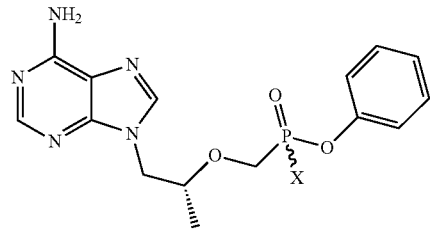

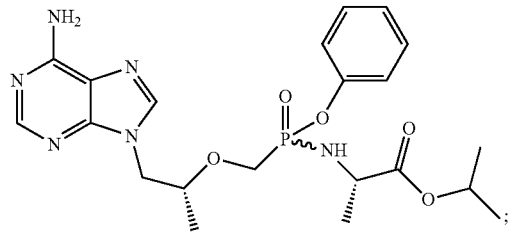

and a method for preparing intermediate compound 12:

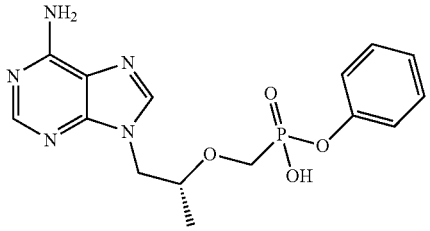

9-{(R)-2-[((S)-{[(S)-1-(isopropoxycarbonyl)ethyl]amino}phenoxyphosphinyl)methoxy]propyl}adenine has anti-viral properties.

7 Claims, No Drawings

METHODS FOR PREPARING ANTI-VIRAL NUCLEOTIDE ANALOGS

CROSS-REFERENCE TO RELATED APPLICATION

This application claims the benefit of priority from U.S. Provisional Patent Application No. 61/544,950, filed Oct. 7, 2011, the content of which is hereby incorporated by reference herein in its entirety.

BACKGROUND OF THE INVENTION

Description of Related Art

U.S. Pat. Nos. 7,390,791 and 7,803,788 (the content of each of which is incorporated by reference herein in its entirety) describe certain prodrugs of phosphonate nucleotide analogs that are useful in therapy. One such prodrug is 9-{(R)-2-[((S)-{[(S)-1-(isopropoxycarbonyl)ethyl]amino}phenoxyphosphinyl)methoxy]propyl}adenine (compound 16):

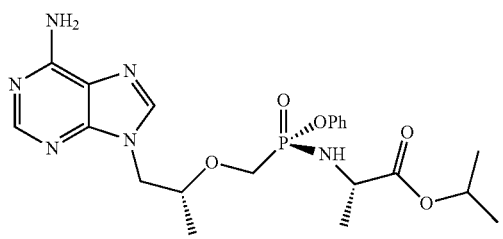

16

This compound is also known by the Chemical Abstract name L-alanine, N-[(S)-[[(1R)-2-(6-amino-9H-purin-9-yl)-1-methylethoxy]methyl]phenoxyphosphinyl]-1-methylethyl ester. U.S. Pat. Nos. 7,390,791 and 7,803,788 also disclose a monofumarate form of this compound and its preparation method (see, e.g., Example 4).

Compound 12, compound 13 (wherein X is halo), and compound 15:

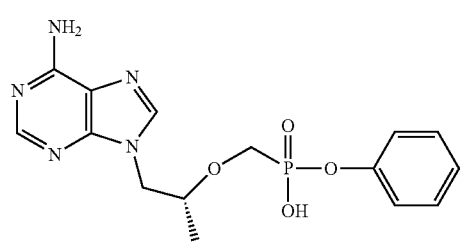

12

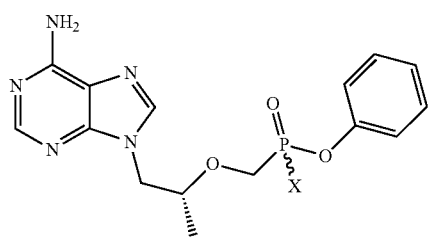

13

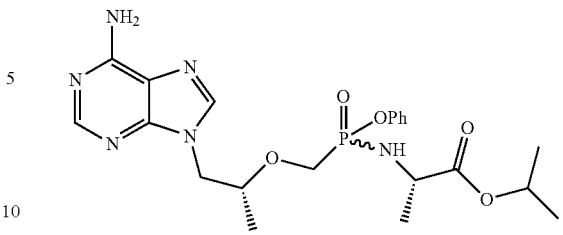

15 are synthetic intermediates that are useful for preparing compound 16. Compound 15 is depicted as a mixture of diastereomers at the phosphorus center. The two diastereomers that make up the mixture of compound 15 are shown here as compounds 15a and 15b. Isomer 15a is identical in structure to compound 16.

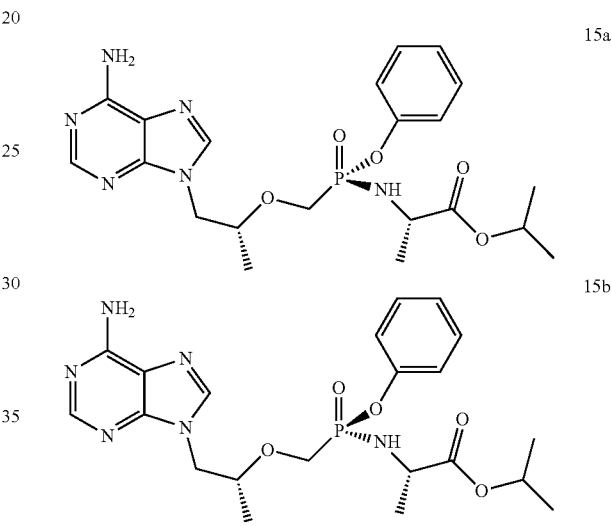

15a

15b

Currently, there is a need for improved methods for preparing compounds 12, 13, 15, and 16. In particular, there is a need for improved methods for preparing compounds 13, 15, and 16 in high diastereomeric purity. Such improved methods may provide higher yields, be easier to perform, or use less costly or toxic reagents than currently available methods.

SUMMARY OF THE INVENTION

Described are an improved method for isolating 9-{(R)-2-[((S)-{[(S)-1-(isopropoxycarbonyl)ethyl]amino}phenoxyphosphinyl)methoxy]propyl}adenine (compound 16) using crystallization-induced dynamic resolution; improved methods for preparing compounds 13 and 15 in high diastereomeric purity; and an improved method for preparing compound 12.

Accordingly, in one embodiment, there is provided a method comprising subjecting a solution comprising: a) a suitable solvent; b) a suitable base; c) the diastereomeric mixture 9-{(R)-2-[((R,S)-{[(S)-1-(isopropoxycarbonyl)ethyl]amino}phenoxyphosphinyl)methoxy]propyl}adenine; and, optionally, d) one or more seed crystals of 9-{(R)-2-[((S)-{[(S)-1-(isopropoxycarbonyl)ethyl]amino}phenoxyphosphinyl)methoxy]propyl}adenine, to conditions that provide for the selective crystallization of 9-{(R)-2-[((S)-{[(S)-1-(isopropoxycarbonyl)ethyl]amino}phenoxyphosphinyl)methoxy]propyl}adenine.

In another embodiment, there is provided a method for preparing compound 13 that is at least about 90% diastereomerically pure by treating a toluene solution of compound 12:

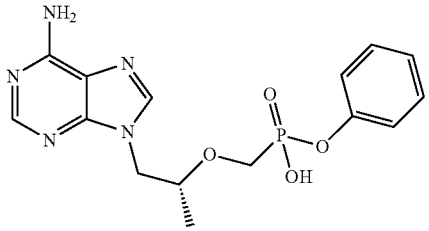

12 with thionyl chloride to provide compound 13, where X=Cl.

In another embodiment, there is provided a method for preparing 9-{(R)-2-[((R,S)-{[(S)-1-(isopropoxycarbonyl)ethyl]amino}phenoxyphosphinyl)methoxy]propyl}adenine (compound 15) that is at least about 90% diastereomerically pure compound 16, comprising treating compound 13:

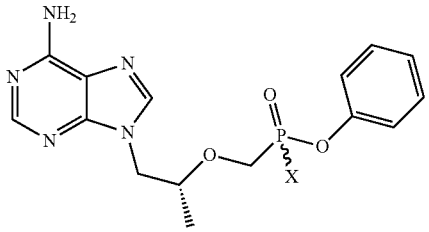

13

(wherein X is halo) that is at least about 90% diastereomerically pure with amine 11:

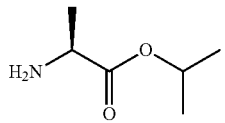

11 under conditions that provide compound 15 that is at least about 90% diastereomerically pure compound 16 (i.e., isomer 15a).

In another embodiment, there is provided a method for preparing compound 12:

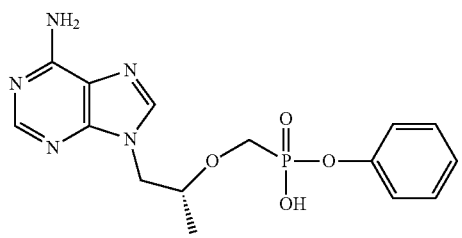

12 comprising treating PMPA:

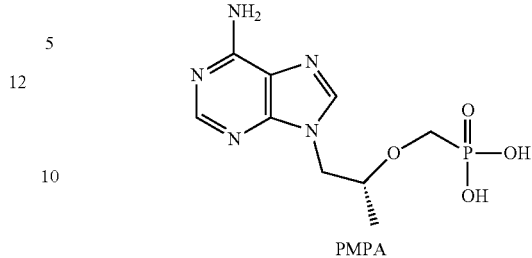

PMPA with triphenylphosphite in the presence of a suitable base to provide compound 12.

Also provided are novel processes and intermediates disclosed herein.

DETAILED DESCRIPTION OF THE INVENTION

Specific values listed below for radicals, substituents, and ranges, are for illustration only; they do not exclude other defined values or other values within defined ranges for the radicals and substituents.

Preparation of Compound 16 by Crystallization-Induced Dynamic Resolution

In one embodiment, there is provided a method for the crystallization-induced dynamic resolution of 9-{(R)-2-[((R,S)-{[(S)-1-(isopropoxycarbonyl)ethyl]amino}phenoxyphosphinyl)methoxy]propyl}adenine (compound 15):

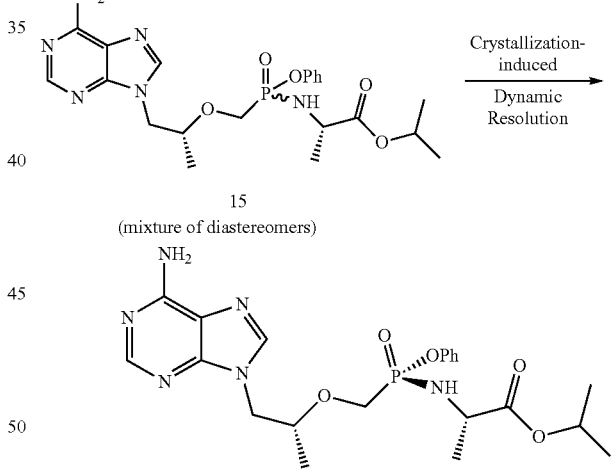

15
(mixture of diastereomers)

16 to provide 9-{(R)-2-[((S)-{[(S)-1-(isopropoxycarbonyl)ethyl]amino}phenoxyphosphinyl)methoxy]propyl}adenine (compound 16). The method comprises subjecting a solution comprising: a) a suitable solvent; b) a suitable base; c) 9-{(R)-2-[((R,S)-{[(S)-1-(isopropoxycarbonyl)ethyl]amino}phenoxyphosphinyl)methoxy]propyl}adenine; and, optionally, d) one or more seed crystals of 9-{(R)-2-[((S)-{[(S)-1-(isopropoxycarbonyl)ethyl]amino}phenoxyphosphinyl)methoxy]propyl}adenine, to conditions that provide for the epimerization of the phosphorus center, under conditions that also provide selective crystallization of 9-{(R)-2-[((S)-{[(S)-1-(isopropoxycarbonyl)ethyl]amino}phenoxyphosphinyl)methoxy]propyl}adenine.

The crystallization can be carried out in any suitable solvent. For example, it can be carried out in an aprotic organic solvent, or in a mixture thereof. For example, the aprotic organic solvent may comprise ethyl acetate, methyl acetate, propyl acetate, isopropyl acetate, diethyl ether, diisopropyl ether, tetrahydrofuran, dichloromethane, acetone, methyl ethyl ketone, methyl tert-butylether, toluene, or acetonitrile, or a mixture thereof. In one embodiment, the solvent comprises acetonitrile.

The resolution can be carried out in the presence of any suitable base. For example, the resolution can be carried out in the presence of a base selected from 1,5-diazobicyclo[4.3.0]non-5-ene (DBN), 1,8-diazabicyclo[5.4.0]undec-7-ene (DBU), 7-methyl-1,5,7-triazabicyclo[4.4.0]dec-5-ene (MTBD), tetramethylguanidine, a Verkade base (e.g., 2,8,9-triisopropyl-2,5,8,9-tetraaza-1-phosphabicyclo[3.3.3]undecane, and 2,8,9-triisobutyl-2,5,8,9-tetraaza-1-phosphabicyclo[3.3.3]undecane), a metal carbonate (e.g., $M_xCO_3$), a metal phenoxide ($M^+$ $^-OPh$), and PhOTMS in combination with a fluoride ion source (e.g., $R_4N^+$ $^-F$, TASF (tris(dimethylamino)sulfonium difluorotrimethylsilicate), or TBAT (tetrabutylammonium triphenyldifluorosilicate), and mixtures thereof, wherein each M is a suitable metal such as an alkali metal or an alkaline earth metal, and each R is, for example, a ($C_1$-$C_6$) alkyl. In one specific embodiment, the base is DBU.

The resolution can also be carried out at any suitable temperature, for example, a temperature in the range of from about 0° C. to about 50° C. In one specific embodiment, the resolution is carried out at a temperature of about 20° C.

In one specific embodiment, the resolution is carried out in the presence of phenol.

The percentage of compound 16 in the starting diastereomeric mixture can be anywhere in the range from about 0% to about 99%. In one embodiment of the invention, the percentage of compound 16 in the starting diastereomeric mixture is in the range from about 0% to about 20%. In one embodiment, the percentage of compound 16 in the starting diastereomeric mixture is in the range from about 20% to about 99%. In one embodiment, the percentage of compound 16 in the starting diastereomeric mixture is in the range from about 50% to about 99%. In one embodiment, the final compound 16 is at least about 90%, about 95%, about 97%, or about 99% diastereomerically pure. In one embodiment, the final compound 16 contains less than 1% of any diastereomeric impurities. In one embodiment, the final compound 16 is free of any detectable diastereomeric impurities.

Preparation of Compound 13 that has High Diastereomeric Purity

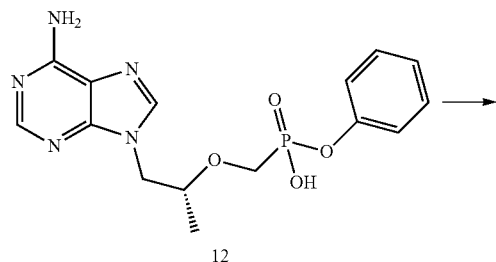

12

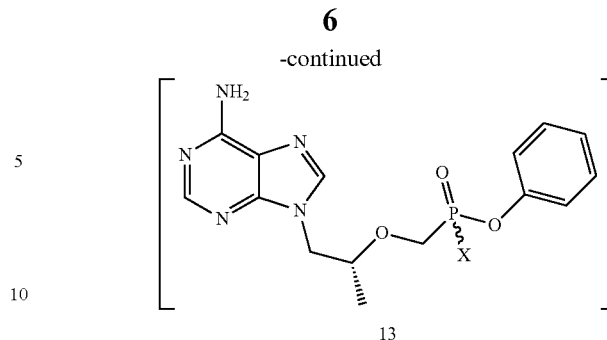

13

Compound 13 (wherein X is halo) that is at least about 90% diastereomerically pure can be prepared by treating compound 12 with a suitable halogenating agent. For example, compound 13 can be prepared by treating compound 12 with a halogenating agent such as, for example, thionyl chloride ($SOCl_2$), oxalyl chloride ($C_2O_2Cl_2$), phosphorus trichloride ($PCl_3$), a chlorotriphenylphosphorane salt, thionyl bromide ($SOBr_2$), oxalyl bromide ($C_2O_2Br_2$), phosphorus tribromide ($PBr_3$), or a bromotriphenylphosphorane salt. The reaction can be carried out in a suitable organic solvent at a suitable temperature (e.g., a temperature in the range from about −20° C. to about 100° C.). Suitable solvents include tetrahydrofuran, 2-methyltetrahydrofuran, dichloromethane, acetonitrile, toluene, chlorobenzene, 1,2-dichloroethane, 1,4-dioxane, sulfolane, and trichloroethylene, and mixtures thereof.

In one embodiment, compound 12 is treated with thionyl chloride in toluene at a temperature of from about 22° C. to about 110° C. to provide compound 13a:

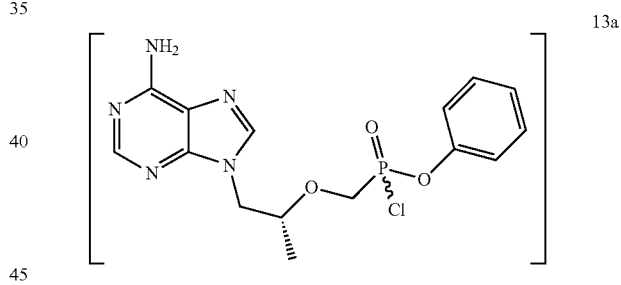

13a that is at least about 90% diastereomerically pure. In one embodiment, the final compound 13a is at least about 90%, about 95%, about 97%, or about 99% diastereomerically pure. In one embodiment, the final compound 13a contains less than 1% of any diastereomeric impurities. In one embodiment, the final compound 13a is free of any detectable diastereomeric impurities.

Preparation of Compound 15 in High Diastereomeric Purity

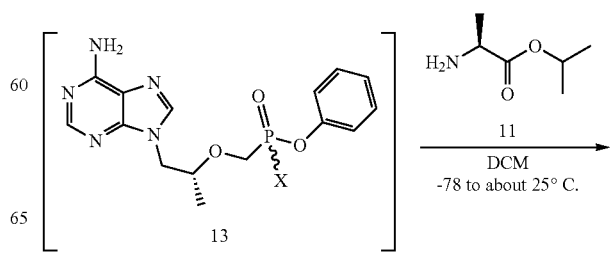

13

-continued

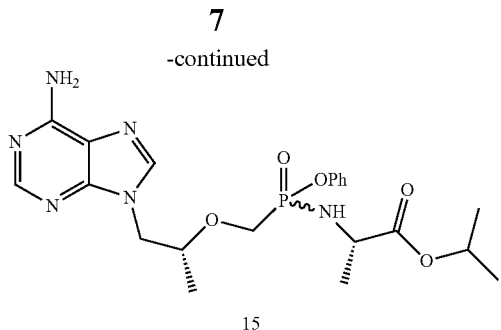

15

Compound 15 can be prepared by treating compound 13 (wherein X is halo) that is at least about 90% diastereomerically pure with amine 11 under conditions that provide compound 15 that is at least about 90% diastereomerically pure in the specific isomer 15a, also represented herein as compound 16. For example, compound 15 can be prepared by treating compound 13 with amine 11 in a suitable organic solvent at a suitable temperature (e.g., a temperature in the range from about −78° C. to about 25° C.). Suitable solvents include organic solvents such as tetrahydrofuran, 2-methyltetrahydrofuran, dichloromethane, 1,2-dichloroethane, trichloroethylene, 1,4-dioxane, acetonitrile, toluene, chlorobenzene, sulfolane, and isopropyl acetate, and mixtures thereof. The reaction conveniently can be carried out in the presence of a suitable base, such as, for example, triethylamine $((C_2H_5)_3N)$, N,N-diisopropylethylamine $([(CH_3)_2CH]_2NC_2H_5)$, or 1,8-bis(dimethylamino)-naphthalene (proton sponge, $C_{14}H_{18}N_2$). Following the reaction, the resulting material can be washed with an aqueous solution containing a suitable wash reagent, such as, for example, sodium phosphate monobasic $(NaH_2PO_4)$, potassium bicarbonate $(KHCO_3)$, citric acid $(C_6H_8O_7)$, or sodium bicarbonate $(NaHCO_3)$. The resulting organic solution can be dried over a suitable drying agent, for example, sodium sulfate, magnesium sulfate, or calcium chloride to provide compound 15 that is at least about 90% diastereomerically pure compound 16.

In one embodiment, compound 13 that is at least about 90% diastereomerically pure (wherein X is chloro) is treated with amine 11 in dichloromethane at a temperature of −25° C. to 25° C. in the presence of triethylamine. The resulting reaction mixture is then washed with an aqueous solution containing sodium phosphate monobasic $(NaH_2PO_4)$ and potassium bicarbonate $(KHCO_3)$ and dried over sodium sulfate to provide compound 15 that is at least about 90% diastereomerically pure compound 16. In one embodiment, the starting compound 13 and resulting compound 15 are at least about 95% or 97% diastereomerically pure. In one embodiment, the final compound 15 contains at least about 90%, about 95%, about 97%, or about 99% diastereomerically pure compound 16. In one embodiment, the final compound 15 contains less than 1% of any diastereomeric impurities.

Preparation of Compound 12

Compound 12 can be prepared as described in, e.g., U.S. Pat. No. 7,390,791, or it can be prepared as described herein. In one embodiment, there is provided a method for preparing compound 12 comprising treating PMPA with triphenylphosphite in the presence of a suitable base to provide compound 12. The reaction conveniently can be carried out in a suitable solvent, such as, for example, acetonitrile, N-methylpyrrolidone (NMP), dichloroethane, pyridine, an alkyl acetate (e.g., ethyl acetate), or a dialkyl ether (e.g., diethyl ether), or a mixture thereof. The reaction conveniently also can be carried out in the presence of a suitable base, such as, for example, a trialkylamine (e.g., triethylamine), 2-methylimidazole, dimethylaminopyridine (DMAP), 1,5-diazobicyclo[4.3.0]non-5-ene (DBN), 1,8-diazabicyclo[5.4.0]undec-7-ene (DBU), or pyridine, or a mixture thereof. The reaction conveniently also can be carried out at a suitable temperature, such as, for example, a temperature from about 20° C. to about 120° C. (e.g., from about 20° C. to about 82° C.). In one specific embodiment, PMPA is treated with triphenylphosphite in the presence of triethylamine and dimethylaminopyridine in acetonitrile at about 80° C. to provide compound 12.

The following are nonlimiting, illustrative Examples.

EXAMPLE 1

Preparation of Diastereomeric Mixture 9-{(R)-2-R[((R,S)-{[(S)-1-(isopropoxycarbonyl)ethyl]amino}phenoxyphosphinyl)methoxy]propyl}adenine (Compound 15)

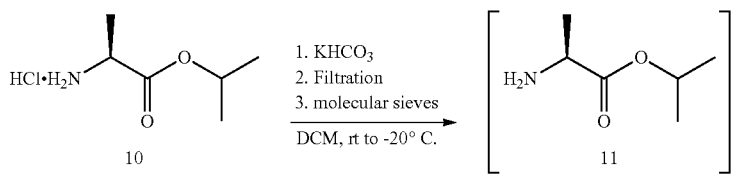

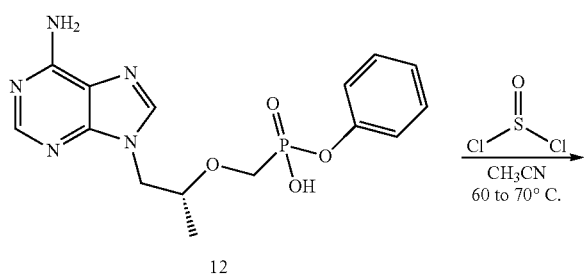

12

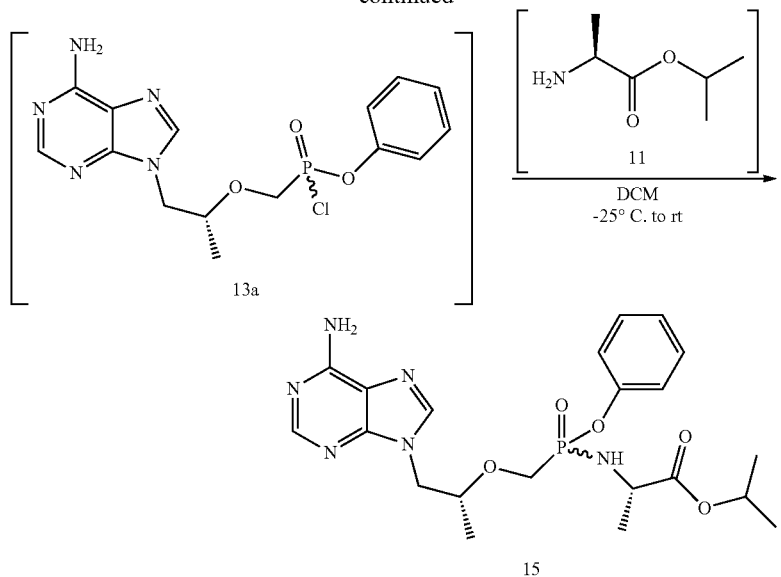

a. Preparation of Compound 11.

Isopropyl L-alanine ester hydrochloride (compound 10) (1 kg, 5.97 mol, 1.0 equiv) and potassium bicarbonate (1.45 kg, 14.5 mol, 2.43 equiv) were agitated in DCM (4 kg) for 10 to 14 hours with maximum agitation, maintaining the pot temperature between 19° C. and 25° C. The mixture was then filtered and rinsed forward with DCM (2 kg). The filtrate was dried over a bed of 4 Å molecular sieves until the water content of the solution was ≤0.05%. The resultant stock solution containing compound 11 was then cooled to a pot temperature of −20° C. and held for further use.

b. Preparation of Compound 13a.

To a solution of thionyl chloride (0.72 kg, 6.02 mol, 2.19 equiv) in acetonitrile (5.5 kg) at 60° C. was added compound 12 (1 kg, 2.75 mol, 1.00 equiv) in 10 equal portions over 2 hours. The pot temperature was then adjusted to 70° C. and stirred for 1 to 3 hours until the reaction was deemed complete. The pot temperature was then adjusted to 40° C. and vacuum applied. The mixture was distilled to dryness, maintaining a maximum jacket temperature of 40° C. The dry residue was then taken up in dichloromethane (30 kg) and the pot temperature adjusted to 19° C. to 25° C. The resultant slurry containing compound 13a was held for further use.

c. Preparation of Compound 15.

To the stock solution of isopropyl L-alanine ester 11 (4.82 equiv) at −25° C. was added slurry containing compound 13a (1.0 equiv) over a minimum of 2 hours, maintaining the pot temperature ≤−10° C. The mixture was then held at a temperature ≤−10° C. for at least 30 minutes, then the pH checked using water wet pH paper. If the pH was <4, adjustment with triethylamine to pH 4-7 was performed. The pot temperature was then adjusted to room temperature (19° C. to 25° C.). In a separate vessel, a solution of sodium phosphate monobasic (2.2 kg, 18 mol, 6.90 equiv) in water (16 kg) was prepared. Half of the sodium phosphate monobasic solution was charged to the phosphonamidate reactor, and vigorously stirred. The layers were settled and partitioned. The organic layer was washed again with the remaining half of sodium phosphate monobasic solution. In a separate vessel, a solution of potassium bicarbonate (1.1 kg, 11 mol, 4.22 equiv) in water (5.5 kg) was prepared. Half of the potassium bicarbonate solution was charged to the organic phase, and vigorously stirred. The layers were settled and partitioned. The organic layer was washed again with the remaining half of the potassium bicarbonate solution, followed by a final water (3.3 kg) wash. The organic phase was then retained and distilled to a volume of approximately 6 L. The resultant solution was analyzed for water content. If the water content was >1.0%, DCM could be charged and the distillation to approximately 6 L repeated. When the solution water content was less than or about 1.0%, the pot temperature was adjusted to 19° C. to 25° C. prior to discharge of the stock solution in DCM to provide the diastereomeric mixture 9-{(R)-2-[((R,S)-{[(S)-1-(isopropoxycarbonyl)ethyl]amino}phenoxyphosphinyl)methoxy]propyl}adenine (compound 15). $^1$H NMR (400 MHz, CDCl$_3$): δ1.20-1.33 (m, 12H), 3.62-3.74 (m, 1H), 3.86-4.22 (m, 5H), 4.30-4.44 (m, 1H), 4.83-5.10 (m, 1H), 6.02 (br s, 3H), 7.18-7.34 (m, 5H), 7.98-8.02 (m, 1H), 8.32-8.36 (m, 1H); $^{31}$P NMR (162 MHz, CDCl$_3$): δ 21.5, 22.9.

EXAMPLE 2

Crystallization-Induced Dynamic Resolution of Diastereomeric Mixture 9-{(R)-2-[((R,S)-{[(S)-1-(isopropoxycarbonyl)ethyl]amino}phenoxyphosphinyl)methoxy]propyl}adenine (Compound 15) to Provide 9-{(R)-2-[((S)-{[(S)-1-(isopropoxycarbonyl)ethyl]amino}phenoxyphosphinyl)methoxy]propyl}adenine (Compound 16)

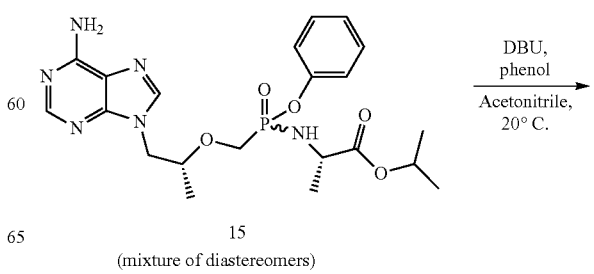

15
(mixture of diastereomers)

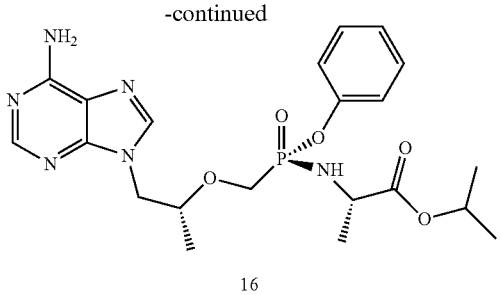

16

A 22 wt % solution of 9-{(R)-2-[((R,S)-{[(S)-1-(isopropoxycarbonyl)ethyl]amino}phenoxyphosphinyl)methoxy]propyl}adenine (compound 15) in acetonitrile (2.3 kg solution, 0.51 kg compound 15, 1.1 mol, equiv) was charged to a vessel equipped with an overhead stirrer, distillation apparatus, and nitrogen inlet. The mixture was concentrated by distillation at 100 to 300 mbar over a temperature range of 45° C. to 55° C. to a final concentration of 30 to 35 wt %. The distillation apparatus was then removed and the solution was cooled to 20° C. The solution was seeded with 2.0% compound 16 and allowed to stir for one hour at 20° C. Phenol (9.9 g, 0.11 mol, 0.1 equiv) and DBU (16 g, 0.11 mol, 0.1 equiv) were added and the mixture was stirred for an additional 24 hours, or until the weight percent of compound 16 remaining in solution was less than 12%. The slurry was then cooled to 0° C. and stirred for an additional 18 hours at 0° C. The slurry was filtered and washed with a 1:1 solution of isopropyl acetate:acetonitrile (1.5 L) at 0° C. The solids were dried in a vacuum oven at 50° C. to give 0.40 kg of compound 16 (80% yield) as a white solid. $^1$H NMR (400 MHz, CDCl$_3$): δ1.21 (m, 9H), 1.28 (d, J=7.0 Hz, 3H), 3.65 (dd, J=13.1, 10.7, 1H) 4.00 (m, 4H), 4.33 (dd, J=14.4, 3.1 Hz, 1H), 5.00 (m, 1H) 6.00 (bs, 2H), 6.99 (m, 2H), 7.07 (m, 1H), 7.19 (m, 2H), 7.97 (s, 1H), 8.33 (s, 1-H). $^{31}$P NMR (162 MHz, CDCl$_3$): δ20.8.

EXAMPLE 3

Preparation of Compound 13a in High Diastereomeric Purity

To a slurry of compound 12 (10.0 g, 27.5 mmol, 1.00 equiv) in toluene (60 mL) at ambient temperature was added thionyl chloride (3.0 mL, 41 mmol, 1.5 equiv). The slurry was heated to 70° C. and agitated for 48 to 96 hours until reaction and diastereomeric enrichment were deemed complete by HPLC (Target: >97.0% conversion of compound 12 to compound 13a and >90:10 diastereomeric ratio of compound 13a). The mixture was concentrated to dryness by vacuum distillation, and the dry residue was taken up in toluene (50 mL). The resultant slurry containing compound 13a was held at ambient temperature for further use.

EXAMPLE 4

Preparation of 9-{(R)-2-[((R,S)-{[(S)-1-(isopropoxycarbonyl)ethyl]amino}phenoxyphosphinyl)methoxy]propyl}adenine (Compound 15) in High Diastereomeric Purity To a solution of isopropyl L-alanine ester 11 (4.50 equiv) in DCM (80 mL) at −25° C. was added a slurry containing compound 13a (1.00 equiv) that is at least 90% diastereomerically pure in toluene (50 mL) over a minimum of 45 minutes, maintaining the internal temperature ≤−20° C. The mixture was then held at a temperature ≤−20° C. for at least 30 minutes, and the pH checked using water wet pH paper. If the pH was <4, it was adjusted with triethylamine to pH 4 to 7. The pot temperature was adjusted to room temperature (19° C. to 25° C.). The mixture was transferred to a separatory funnel and washed sequentially with 10% w/v aqueous solution of sodium phosphate monobasic (2×50 mL), 15% w/v aqueous solution of potassium bicarbonate (2×20 mL), and water (50 mL). The final organic layer was dried over anhydrous sodium sulfate, filtered, and concentrated in vacuo to a viscous amber oil. The oil was dissolved in toluene/acetonitrile (4:1) (50 mL), and the solution was seeded with 9-{(R)-2-[((R,S)-{[(S)-1-(isopropoxycarbonyl)ethyl]amino}phenoxyphosphinyl)methoxy]propyl}adenine (about 1 mg, 99:1 diastereomeric ratio) and stirred for 2 hours at ambient temperature. The resultant slurry was filtered and the filter cake was washed with toluene/acetonitrile (4:1) (15 mL) and dried in a vacuum oven at 40° C. for 16 hours to give the product, 9-{(R)-2-[((R,S)-{[(S)-1-(isopropoxycarbonyl)ethyl]amino}phenoxyphosphinyl)methoxy]propyl}adenine (compound 15), as a white solid (10.0 g, 76.4%, 97.5:2.5 diastereomeric ratio in favor of compound 16). $^1$H NMR (400 MHz, CDCl$_3$): δ1.20-1.33 (m, 12H), 3.62-3.74 (m, 1H), 3.86-4.22 (m, 5H), 4.30-4.44 (m, 1H), 4.83-5.10 (m, 1H), 6.02 (br s, 3H), 7.18-7.34 (m, 5H), 7.98-8.02 (m, 1H), 8.32-8.36 (m, 1H); $^{31}$P NMR (162 MHz, CDCl$_3$): δ21.5, 22.9.

EXAMPLE 5

Preparation of Compound 12

PMPA (100.0 g, 0.35 mol, 1 equiv) was charged to a vessel equipped with an overhead stirrer, reflux condenser, and nitrogen inlet, followed by acetonitrile (800 mL). To the vessel was added triethylamine (71.0 g, 0.70 mol, 2 equiv) followed by DMAP (42.6 g, 0.35 mol, 1 equiv) and triphenylphosphite (162.1 g, 0.52 mol, 1.5 equiv). The mixture was heated to 80° C. and agitated for ≥48 hours at 80° C. or until the reaction was complete by $^{31}$P NMR. (A sample directly from the reaction is taken and an insert containing 10% H$_3$PO$_2$ in D$_2$O is added. The intermediate formed is the PMPA anhydride and is at 7 to 8 ppm; the product is at 12.3 to 12.6 ppm. The reaction is deemed complete when less than 5% anhydride is present). The reaction mixture was distilled to approximately 1.5 volumes of acetonitrile and diluted with ethyl acetate (200 mL) and water (300 mL). The aqueous layer was separated and washed with ethyl acetate (200 mL) twice. The aqueous layer was recharged to the vessel and pH adjusted to pH 3 using 12.1 M HCl (21.0 mL). The reaction was then seeded with 0.05% of compound 12 and allowed to stir at 25° C. An additional 12.1 M HCl was added over 20 minutes (7.0 mL) until pH 2 was achieved. The crystallization was allowed to stir at ambient temperature for 30 minutes and then cooled to 10° C. over 2 hours. Once at 10° C., the crystallization was allowed to stir for 2.5 hours at 10° C. The slurry was filtered and washed with pH 1.5 water (200 g). After drying in the vacuum oven, 102.2 g of compound 12 (81% yield) was obtained as a white solid. $^1$H NMR (400 MHz, D$_2$O): δ1.31 (d, J=6.1 Hz, 3H), 3.59 (dd, J=14.0, 9.0 Hz, 1H), 3.85 (dd, J=14.0, 9.0 Hz, 1H), 4.1 (m, 1H), 4.3 (dd, J=15.0, 9.0 Hz, 1H), 4.5 (dd, J=15.0, 2 Hz, 1H), 6.75 (d, J=7 Hz, 2H), 7.15 (t, J=7 Hz, 1H), 7.25 (t, J=7 Hz, 2H), 8.26 (s, 1H), 8.35 (s, 1H). $^{31}$P NMR (162 MHz, D$_2$O): δ14.8.

All publications, patents, and patent documents are hereby incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for the selective crystallization of 9-{(R)-2-[((S)-{[(S)-1-(isopropoxycarbonyl)ethyl]amino}phenoxyphosphinyl)methoxy]propyl}adenine, comprising the steps of:
    subjecting at 0-50° C. a solution comprising:
    a) a suitable solvent;
    b) a suitable base; and
    c) 9-{(R)-2-[((R,S)-{[(S)-1-(isopropoxycarbonyl)ethyl]amino}phenoxyphosphinyl)methoxy]propyl}adenine, to crystallization-induced dynamic resolution using a seed crystal of 9-{(R)-2-[((R,S)-{[(S)-1-(isopropoxycarbonyl)ethyl]amino}phenoxyphosphinyl)methoxy]propyl}adenine under conditions that provide for the epimerization of the phosphorous center.

2. The method of claim 1, wherein the solvent comprises an aprotic organic solvent.

3. The method of claim 1, wherein the solvent comprises ethyl acetate, methyl acetate, propyl acetate, isopropyl acetate, diethyl ether, diisopropyl ether, tetrahydrofuran, dichloromethane, acetone, methyl ethyl ketone, methyl tert-butylether, toluene, or acetonitrile, or a mixture thereof.

4. The method of claim 3, wherein the solvent comprises acetonitrile.

5. The method of claim 1, wherein the base is 1,5-diazobicyclo[4.3.0]non-5-ene; 1,8-diazabicyclo[5.4.0]undec-7-ene; 7-methyl-1,5,7-triazabicyclo[4.4.0]dec-5-ene; tetramethylguanidine; a Verkade base; a metal carbonate; a metal phenoxide; or PhOTMS in combination with a fluoride ion source; or a mixture thereof.

6. The method of claim 5, wherein the base is 1,8-diazabicyclo[5.4.0]undec-7-ene.

7. The method of claim 1, wherein the solution further comprises phenol.

* * * * *